United States Patent [19]
Kelman

[11] Patent Number: 5,769,889
[45] Date of Patent: Jun. 23, 1998

[54] HIGH MYOPIA ANTERIOR CHAMBER LENS WITH ANTI-GLARE MASK

[76] Inventor: Charles D. Kelman, 721 Fifth Ave., New York, N.Y. 10022

[21] Appl. No.: 708,467

[22] Filed: Sep. 5, 1996

[51] Int. Cl.⁶ ...................................................... A61F 2/14
[52] U.S. Cl. ................................................................ 623/6
[58] Field of Search ................................................... 623/6

[56] References Cited

U.S. PATENT DOCUMENTS

| | | | |
|---|---|---|---|
| 4,124,905 | 11/1978 | Clark | 623/6 |
| 4,573,998 | 3/1986 | Mazzocco | 623/6 |
| 4,638,056 | 1/1987 | Callahan et al. | 623/6 X |
| 4,657,546 | 4/1987 | Shearing | 623/6 |
| 4,676,791 | 6/1987 | LeMaster et al. | 623/6 |
| 4,693,716 | 9/1987 | Mackool | 623/6 |
| 4,764,169 | 8/1988 | Gendahl | 623/6 |
| 4,769,035 | 9/1988 | Kelman | 623/6 |
| 4,808,181 | 2/1989 | Kelman | 623/6 |
| 4,911,715 | 3/1990 | Kelman | 623/6 |
| 5,026,396 | 6/1991 | Darin | 623/6 |
| 5,133,750 | 7/1992 | Momose et al. | 623/6 |
| 5,275,624 | 1/1994 | Hara et al. | 623/6 |

FOREIGN PATENT DOCUMENTS

| | | | |
|---|---|---|---|
| 165652 | 12/1985 | European Pat. Off. | 623/6 |
| 3503690 | 11/1986 | Germany | 623/6 |

*Primary Examiner*—Mary Beth Jones
*Attorney, Agent, or Firm*—Darby & Darby

[57] ABSTRACT

A two piece anterior chamber artificial intraocular lens for treating high myopia conditions by implantation in an eye after extracapsular removal of the natural eye lens is disclosed. The two-piece assembly is inserted through a minimum size incision in the eye. The lens includes a lens body or optic and a separate ring-shaped tension frame therefor containing light masking means for inhibiting light rays directed toward the outer edge portions of the lens body from being scattered thereby toward the retina after the assembled lens has been inserted into the eye. The lens body or optic is generally circular and conveniently made of shape retaining plastic. The optic is generally smaller than the diameter of a pupil dilated for night vision, and is surrounded by a snugly fitting annular opaque or semi-opaque ring or frame having a C-shaped cross section and a peripherally extending fin of the same material. The fin is preferably formed of flexible material which is bent during insertion to allow insertion of the two-piece assembly through a minimal size corneal incision. The lens is also provided with position fixation means, such as haptics, which are integrally formed with the lens body and extend outward in the generally horizontal plane of the lens body for seating the lens in the eye. The ring-shaped frame is preferably mated with the lens during manufacturing.

21 Claims, 2 Drawing Sheets

HIGH MYOPIA ANTERIOR CHAMBER LENS WITH ANTI-GLARE MASK

FIELD OF THE INVENTION

The present invention generally relates to the field of intraocular lenses. More specifically, the present invention is for an anterior chamber intraocular lens which is capable of being inserted through a small incision in the eye and which does not cause any appreciable glare.

BACKGROUND OF THE INVENTION

For treating conditions such as natural eye lens cataracts, a known eye surgery procedure is to remove the cataracted lens through a minimum size incision in the wall of the cornea of the eye, and replace it with an implanted artificial intraocular lens. The implantation of an intraocular lens is a well known and widely used technique for restoring vision after cataract surgery. The natural structure of the eye furnishes a variety of locations for fixing the position of the intraocular lens in the eye. For example, the intraocular lens can be supported anteriorly of the iris, between the scleral spur and the iris. Alternatively, an intraocular lens can be supported posteriorly of the iris. In practice, anterior chamber lenses are simpler to implant because the anterior chamber angle can be viewed by the surgeon while he seats the lens within the eye. Conversely, posterior chamber lenses are more difficult to implant, since they are seated behind the iris.

To minimize the possibility of injury to the eye, it is important that the incision be made as small as possible. However, the size of the incision is generally dictated by the size of the artificial lens which is to be implanted. To allow for proper nighttime vision, the artificial lens must be sufficiently large to cover the pupil when it is dilated.

Additionally, the artificial lens should not cause any glare. Glare is caused when light passes through an edge or boundary between regions which are both substantially transparent. Conversely, there is no glare when light passes through an edge or boundary between two regions where at least one of the regions is substantially opaque. One example of this latter situation is the boundary formed by the iris at its inner edge defining the pupil. The iris surrounding the pupil is substantially opaque, while the pupil is substantially transparent to allow the passage of light to the retina.

Glare may be eliminated by making the artificial lens, which is substantially transparent to light, larger than the size of the dilated pupil. In this way, there are no edges or boundaries visible when the pupil is dilated. However, this results in a fairly large artificial lens requiring a correspondingly large incision in the cornea wall.

One approach to reducing glare while at the same time reducing the size of the incision in the cornea is to construct the artificial lens from several pieces which are joined together after the individual pieces are inserted through the corneal incision. In this way, the corneal incision may be made relatively small, while the resulting artificial lens is sufficiently large to properly perform its intended function. One example of a multi-piece intraocular lens is disclosed in my earlier U.S. Pat. No. 4,911,715 issued Mar. 27, 1990, which is incorporated herein by reference. The disclosed intraocular lens is implanted in the posterior chamber and includes a lens body and a separate ring-shaped collapsible filament and tension frame. The frame further includes light masking material. The lens and frame are inserted separately into the corneal incision and then joined together by inserting tabs on the lens body into opposite receiving slits located on the frame. After insertion of the lens body into the frame, the light masking material on the frame is positioned over the edges of the lens body so as to inhibit light rays directed toward the lens body outer edge portions from being scattered thereby.

Another example of a multi-piece intraocular lens is disclosed in my earlier U.S. Pat. No. 5,074,876 issued Dec. 24, 1991, which is incorporated herein by reference. The disclosed intraocular lens is implanted in the posterior chamber and includes an oblong lens body and a collapsible ring-shaped tension frame for receiving the lens body after both elements are inserted through the corneal incision. The tension frame includes a pair of light masking wing elements located along the longer dimension of the frame. The light masking elements are connected to each other at their ends by a pair of filaments, each filament connecting one corner of a light masking element to a corner of the other light masking element. The lens body is tensionally seated within the frame by way of grooves formed in the shorter sides of the lens body which engage the filaments interconnecting the light masking elements. The lens is also positionally maintained with respect to the light masking elements through a coacting seating arrangement.

An alternative approach to intraocular lens design which results in a non-glare producing lens and which requires a small incision is to include a masking portion at the periphery of the lens. One example of this type of intraocular lens is described in my earlier U.S. Pat. No. 4,605,409 issued Aug. 12, 1986, which is incorporated herein by reference. The intraocular lens described therein is implanted in the posterior chamber and includes a deformable or moveable pair of masking means integrally attached or connected to the lens body. Each member of the masking means is moveable between a contracted position which facilitates insertion through an incision in the eye, and an expanded position which is attained after insertion. In the contracted position, each member of the masking means is pivoted to a position underneath the lens body. In the expanded position, each member is pivoted out to a position adjacent to and overlapping slightly with the peripheral edge of the lens body, thereby functioning to reduce or eliminate glare.

My earlier U.S. Pat. No. 4,833,890 issued May 30, 1989, which is incorporated herein by reference, discloses an intraocular lens which is implanted in the posterior chamber and has a lens body tensionally mounted within a ring-shaped frame. The frame includes contractible peripheral light masking wings which surround the lens body. To facilitate insertion into the eye through a relatively small corneal incision, the light masking wings, which are formed from a resilient material, are folded under the lens body. Once the intraocular lens has been inserted into the eye, the light masking wings are unfolded and assume their expanded shape whereby the light masking wings cover the peripheral edges of the lens body, thereby reducing or eliminating any glare. The intraocular lens also includes a pair of opposed position fixation means or haptics connected to the ring-shaped frame for properly seating the lens in the eye.

Intraocular lenses for high myopia conditions generally have a thickened peripheral portion. However, as the diameter of the lens is increased so as to avoid glare conditions, there is a danger that the thickened peripheral portion will come in contact with the inner surface of the cornea, resulting in potential injury. Alternatively, the diameter of the optic or lens body may be reduced in order to avoid the above-mentioned peripheral contact. However, in this latter situation, the optic will be smaller than the pupil in its dilated condition, resulting in glare caused by the light being reflected from the edge of the smaller diameter optic.

It would be desirable to provide a minimum size intraocular lens for implantation in the eye following extracapsular removal of the natural eye lens, permitting rapid and efficient lens insertion through the same minimum size corneal incision used to remove the natural lens. Additionally, it is desirable to provide light masking means for the lens body, while utilizing a structurally simple arrangement of parts which are readily fabricated at relatively low cost using widely available materials. Moreover, it would be desirable to provide a minimum size intraocular lens which does not touch the inner surface of the cornea, while at the same time not causing any glare.

OBJECTS OF THE INVENTION

One of the objects and advantages of the present invention is to overcome the drawbacks and inefficiencies of the prior art, and to provide a two piece artificial intraocular lens for insertion of the two-piece assembly through a minimum size incision into the eye for implantation, e.g., after extracapsular removal of the natural eye lens.

It is an additional object of the present invention to provide an anterior chamber two piece intraocular lens of minimum insertion width and having individual pieces permitting maximum accommodation of a small size optic through a minimum size eye incision, in addition to a frame therefor which does not require an incision substantially larger than that which is needed for the optic. The two-piece assembly can be rapidly and efficiently inserted into the eye, and then implanted, and still provide light masking for the optic.

It is a further object of the present invention to provide a two piece anterior chamber intraocular lens which is readily fabricated at relatively low cost from widely available materials having desired characteristics, and which utilizes a structurally simple arrangement of cooperating parts.

It is yet another object of the present invention to provide a two piece anterior chamber intraocular lens for treating high myopia conditions, and which does not present the danger of contacting the inner surface of the cornea, while at the same time not causing any glare.

SUMMARY OF THE INVENTION

The present invention relates to a two piece anterior chamber intraocular lens, and more particularly to an artificial intraocular lens for treating high myopia conditions by implantation in an eye, such as in the anterior chamber, after extracapsular removal of the natural eye lens. The two-piece assembly is inserted through a minimum size incision in the eye. The lens includes a lens body or optic and a separate ring-shaped tension frame therefor containing light masking means for inhibiting light rays directed toward the outer edge portions of the lens body from being scattered thereby toward the retina after the assembled lens has been inserted into the eye.

The lens body or optic is generally circular and has a maximum diameter of approximately 3.5 to 5.0 millimeters. The lens body, or optic, is conveniently made of shape retaining plastic. The optic is generally smaller than the diameter of a pupil dilated for night vision, and is surrounded by a snugly fitting annular opaque or semi-opaque ring or frame having a C-shaped cross section and a peripherally extending fin of the same material. The lens is also provided with position fixation means, such as haptics, which are integrally formed with the lens body and extend outward in the generally horizontal plane of the lens body for seating the lens in the eye. The haptics and lens body are preferably made of polymethylmethacrylate (PMMA).

The frame is a generally circular shaped element having a C-shaped cross section member which provides a groove on the inner circumference of the frame for receiving the lens body. Integrally formed with the C-shaped cross section member of the frame is a thin, preferably annular fin extending radially outward of the C-shaped cross section member. The frame is also provided with radially extending notches or slots equal in number to the number of haptics used for seating the lens. The radial slots provide passageways for connecting the haptics to the lens body. The C-shaped cross section member and annular fin are preferably formed of optically opaque or translucent material in order to function as light masking means. The frame is preferably made of silicone and is preferably snapped onto the optic during manufacturing. During insertion into the eye, the flexible fin is folded or bent so as to facilitate insertion of the assembled two-piece assembly into the eye through a minimal size corneal incision. Once the two-piece assembly is inserted into the eye, the fin returns to its original radially outwardly extending position.

BRIEF DESCRIPTION OF THE DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which.

DETAILED DESCRIPTION OF THE PREFERRED EMBODIMENTS

Figure 1:
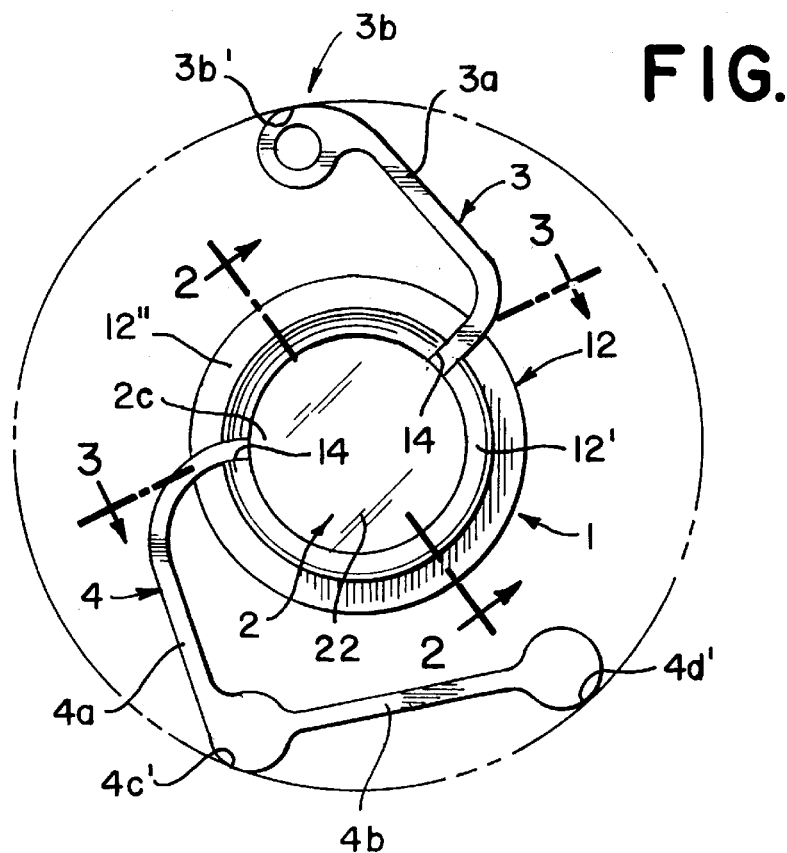
FIG. 1 is a plan view of an embodiment of an intraocular lens according to the present invention intended for fixation in the anterior chamber of the eye.
Figure 3:
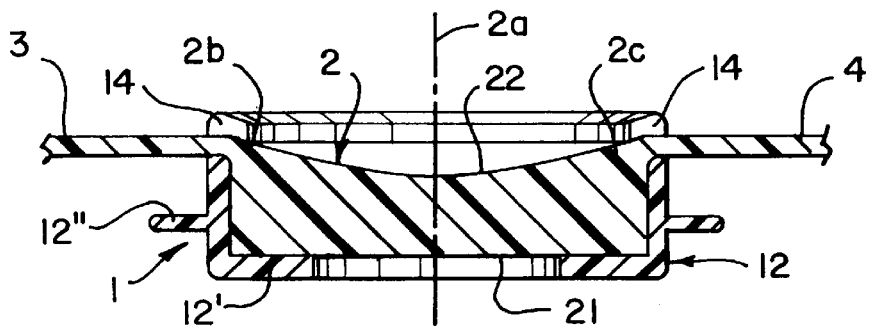
FIG. 3 is a cross sectional view of the intraocular lens of FIG. 1 taken along the line 3—3.

Referring now to FIG. 1, therein is shown an anterior chamber intraocular lens 1 having a central optic portion 2 with an optical axis 2a (shown in FIG. 3). Extending from a first peripheral portion 2b of the optic 2 is a first fixation element 3. The optic has a second peripheral portion 2c spaced from said first mentioned peripheral portion and generally at opposite sides of the optical axis 2a with respect to said first mentioned peripheral portion. Extending from said second peripheral portion 2c of optic 2 is a second position fixation element 4. The position fixation elements 3, 4 extend from the optic 2 generally tangentially and in generally opposite directions with respect to each other.

According to the aforesaid construction, there is formed an anterior chamber lens 1 which exhibits three-point fixation capability. One or both of the position fixation elements, or legs, 3 and 4 is resilient i.e., springy, such that it will return to its original undeformed condition shown in FIG. 1 after compression of extension away from the illustrated configuration. The anterior chamber lens according to the instant invention has the important capability of being able to be deformed in such manner and to such an extent as to be safely and easily accommodated in anterior chamber angles having a wide range of diameters. Thus, according to the preferred embodiment of the instant invention, the optic 2 and the haptics 3 and 4 are manufactured as a unit, of a single piece of polymethylmethacrylate (PMMA), or similar biologically inert plastic material. Alternatively, the elements 3, 4 may be connected by adhesive or ultrasonic welding or any other connection method known in the art. The cross-sectional shape, diameter and length of the position fixation elements 3 and 4 as well as the angles at which they project from optic 2 and the amount of curvature of the legs 3a and 4a are all such as to facilitate a combined flexure of those elements sufficient to permit substantial relative movement between contact surfaces 4c' and 4d', on the one hand, and contact surface 3b' on the other hand.

Figure 2:
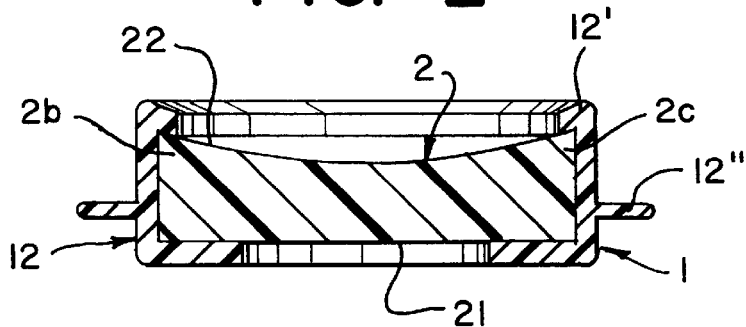
FIG. 2 is a cross sectional view of the intraocular lens of FIG. 1 taken along the line 2—2.

Referring now to FIG. 2, there is shown a cross section of the intraocular lens 1 according to the present invention. Lens 1 includes a lens body 2 and a ring-shaped tension frame 12 surrounding and holding the lens body 2. The lens body 2 is generally circular and has a maximum diameter of approximately 3.5 to 5.0 millimeters. Lens body 2 is advantageously suited for patients suffering from high myopia. Accordingly, lens body 2 has a generally flat face 21 (the posterior face) and a generally concave face 22 (the anterior face). The lens body 2 may be made of shape retaining plastic. Frame 12 is generally circular and has a C-shaped cross section portion 12' which provides a groove on the inner circumference of the frame 12 for receiving and retaining the lens body 2. Integrally formed with the C-shaped cross section portion 12' is an annular shaped fin 12" extending radially outward. Fin 12" preferably extends 0.3 to 1.0 millimeters radially outwardly and is typically not centered with respect to the cylindrical edge of the lens body 2. Rather, fin 12" is located at a horizontal plane which is perpendicular to the optical axis 2a, but which is located approximately 0.5 to 1.0 millimeters closer to the posterior face 21 than to the horizontal plane passing through the anterior peripheral edge of lens body 2. Frame 12 is preferably formed of silicone.

The relatively small diameter of lens body 2 facilitates insertion into the eye via a comparatively smaller corneal incision. The addition of frame 12 surrounding lens body 2 reduces glare associated with light passing through lens 1. To achieve this effect, frame 12 is preferably formed of optically opaque or translucent material, such as silicone, in order to function as a light masking means at the periphery of the lens body 2. Lens 1 is particularly suited for high myopia conditions, and as such, is greater in thickness at its peripheral portion than at its center portion. Normally, in order to avoid glare resulting from light impinging on the peripheral edge of the optic, the optic is formed slightly larger in diameter than the diameter of the fully dilated pupil. This type of construction, however, risks the possible scratching of the inner corneal surface due to the wide diameter and increased thickness of the high myopia lenses at the peripheral portion thereof. Unfortunately, the thickened peripheral portion must be positioned just in the region of the eye where the clearance is reduced due to the curvature of the cornea. However, the lens of the present invention substantially reduces these problems while at the same time still providing an intraocular lens suitable for high myopia conditions. The reduced diameter of the lens according to the present invention positions the increased peripherally thick portion of the lens closer to the center of the eye where there is substantially more clearance. Thus, the risk of scratching the inner corneal surface is reduced. Moreover, the addition of frame 12 substantially eliminates any glare normally associated with a reduced diameter lens.

Figure 4A:
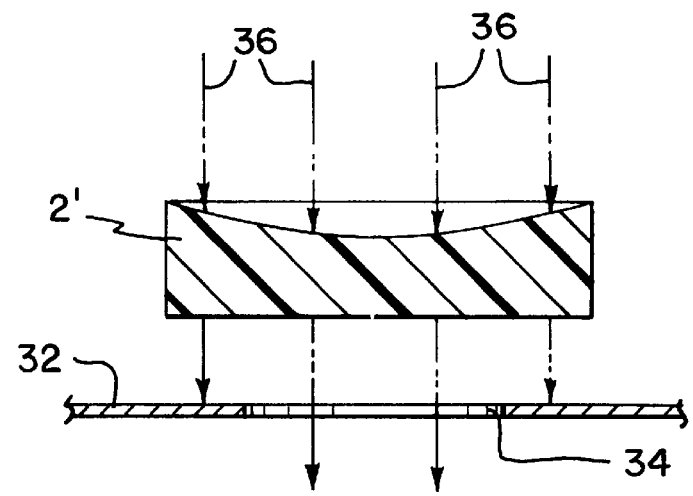
FIGS. 4a is an illustration showing incident light passing through a conventional lens positioned in front of a constricted iris.
Figure 4B:
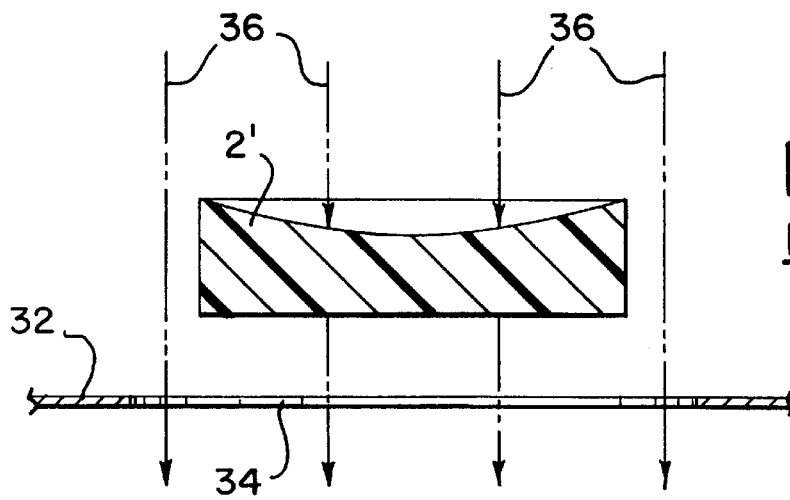
FIG. 4b is an illustration showing incident light passing through a conventional lens positioned in front of a dilated iris.
Figure 4C:
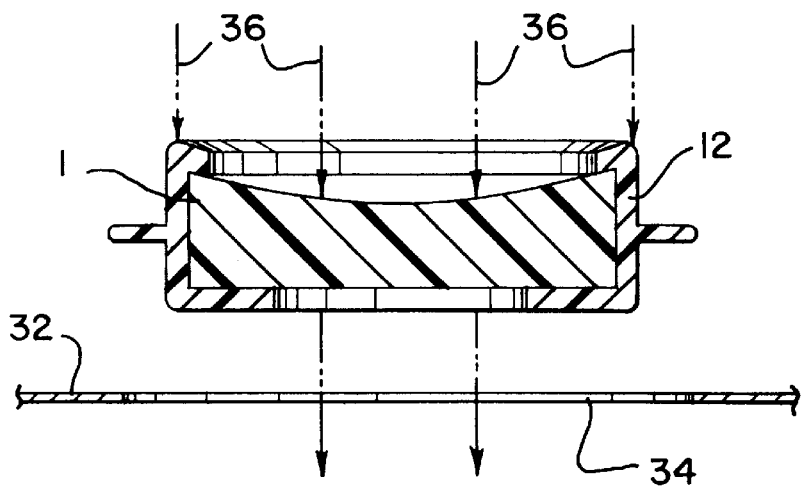
FIG. 4c is an illustration of a lens according to the present invention positioned in front of a dilated iris.

FIGS. 4a—4c illustrate how the reduced diameter of the lens according to the present invention is used to substantially eliminate glare. Referring now to FIG. 4a, a conventional lens 2' is positioned in front of an iris 32, which is in a constricted state. Because iris 32 is in a constricted state, the iris aperture 34 is smaller in diameter than the diameter of lens 2'. Accordingly, there is no glare effect since none of the impinging light rays 36 which pass through the aperture 34 pass through the peripheral edge of lens 2'. In contrast, FIG. 4b shows a conventional lens 2' positioned in front of a dilated iris 32. Under these conditions, some of the incident light rays 36 which pass through the aperture 34 also pass near the peripheral edge of the lens 2', resulting in a perceived glare.

FIG. 4c shows the lens 1 of the present invention positioned in front of a dilated iris 32. As shown in FIG. 4c, the incident light rays 36 which pass near the peripheral edge of the lens 1 are impeded from reaching the iris aperture 34 because of the presence of frame 12 which acts as a light masking means. In this way, although the diameter of lens 1 is smaller than the diameter of the aperture 34 caused by the dilated iris 32, nevertheless, there is no glare because of the light masking effect of the frame 12.

Frame 12 is also provided with radially extending notches or slots 14 (FIG. 3) for the haptics or position fixation members 3 and 4. The radial slots 14 provide passageways for the haptics 3, 4, which are integral with the lens body 2. Alternatively, the haptics 3, 4 may be integrally formed with the frame 12. In this latter embodiment, the radial slots 14 would not be needed.

Insertion of the lens 1 according to the present invention is accomplished by inserting the lens assembly 1, i.e., the lens body 2 and frame 12, via the corneal incision. During insertion into the eye, the thin, flexible fin 12" is folded or bent towards the lens body 2 so as to facilitate insertion of the two-piece lens assembly 1 into the eye through a minimal size corneal incision. Once the two-piece assembly 1 is inserted into the eye, the fin 12" returns to its original position extending radially outward of the lens body 2 and C-shaped cross section member 12'. In this way, the two-piece lens assembly 1 is inserted through a corneal incision which is only slightly larger than that needed for the lens body 2. The two piece construction of lens 1 having a resilient fin facilitates exploitation of the minimum size corneal incision used by the surgeon for extracapsular removal of the natural eye lens. This is particularly significant since, understandably, the smaller the corneal incision size the less trauma experienced by the patient, and in turn, the less the pain and discomfort endured then and thereafter, not only because of the incision itself but also because of the number and/or size of any needed sutures.

While the invention has been particularly shown and described with reference to a preferred embodiment thereof, it will be understood by those skilled in the art that various changes in form and details may be made therein without departing from the spirit and scope of the invention.

What is claimed is:

1. A two piece intraocular lens assembly for insertion of the two-piece assembly through a minimum size incision into the eye for implantation in the eye, comprising:

a generally circular high myopia optic member having a first face and a second, concave face forming a thickened peripheral optic region;

a ring-shaped frame member having a radially inward enclosing C-shaped cross section providing an inner circumferential groove for receiving and holding the thickened peripheral optic region of said optic member, and an annular fin extending radially outward from said C-shaped member, said annular fin having a diameter at least as large as a diameter of a dilated pupil of the eye, said annular fin being made of substantially flexible material, whereby said annular fin may be bent in a radially inward direction during insertion of the lens assembly into the eye while the ring-shaped frame member securely holds the optic member; and a pair of lateral position fixation means connected with one of said members to position the two-piece lens assembly within the eye.

2. A lens assembly according to claim 1, wherein said annular fin is substantially optically opaque.

3. A lens assembly according to claim 1, wherein said annular fin is substantially optically translucent.

4. A lens assembly according to claim 1, wherein said ring-shaped frame member is substantially optically opaque.

5. A lens assembly according to claim 1, wherein said ring-shaped frame member is substantially optically translucent.

6. A lens assembly according to claim 1, wherein said lens assembly is adapted to be positioned away from an inner corneal surface.

7. A lens assembly according to claim 1, wherein said annular fin is integrally formed with said ring-shaped frame member.

8. A lens assembly according to claim 1, wherein an innermost diameter of said frame member is in the range of 3.5 to 5.0 millimeters and said annular fin extends radially outwardly from the outer periphery of said frame member 0.3 to 1.0 millimeters.

9. A lens assembly according to claim 8, wherein said annular fin is located in a plane perpendicular to an optical axis of said optic member, said plane being positioned closer to said first face of said optic member than to said concave face by a predetermined distance in the range of 0.5 to 1.0 millimeters.

10. A lens assembly according to claim 1, wherein said optic member is comprised of PMMA material and said frame member is comprised of silicone material.

11. A lens assembly according to claim 1, wherein each of the pair of lateral position fixation means includes:

a position fixation element extending from the optic member.

12. A lens assembly according to claim 11, wherein the optic member is monolithically integrated with each position fixation element.

13. A lens assembly according to claim 11, wherein each position fixation element is composed of PMMA material and the frame member is composed of silicone material.

14. A lens assembly according to claim 1, wherein said second concave face extends to and slopes radially inwardly from said thickened peripheral optic region; and wherein the inner circumferential groove of the C-shaped cross section extends around said thickened peripheral optic region to receive and grasp the radially inwardly sloping peripheral region of said concave face.

15. A two piece intraocular lens assembly for insertion of the two-piece assembly through a minimum size incision into the eye for implantation in the eye, comprising:

a generally circular high myopia optic member having a first face and a second, concave face forming a thickened peripheral optic region;

a ring-shaped frame member having a radially inward enclosing C-shaped cross section providing an inner circumferential groove for receiving and holding said thickened peripheral optic region of said optic member, and an annular fin extending radially outward from said C-shaped member, said annular fin having a diameter at least as large as a diameter of a dilated pupil of the eye, said annular fin being made of substantially flexible material, whereby said annular fin may be bent in a radially inward direction during insertion of the lens assembly into the eye while the ring-shaped frame member securely holds the optic member; and a pair of lateral position fixation members monolithically integral with the optic member to position the two-piece lens assembly within the eye.

16. A lens assembly according to claim 15, wherein a portion of the ring-shaped frame member is substantially optically opaque.

17. A lens assembly according to claim 15, wherein a portion of the ring-shaped frame member is substantially optically translucent.

18. A two piece intraocular lens assembly for insertion of the two-piece assembly through a minimum size incision into the eye for implantation in the eye, comprising:

a lens member including:

a generally circular high myopia optic member having a first face and a second, concave face forming a thickened peripheral optic region; and a pair of lateral position fixation members extending from the optic member to position the two-piece lens assembly within the eye; and a ring-shaped frame member having a radially inward enclosing C-shaped cross section providing an inner circumferential groove for receiving and holding the thickened peripheral optic region of said optic member, and an annular fin extending radially outward from said C-shaped member, said annular fin having a diameter at least as large as a diameter of a dilated pupil of the eye, said annular fin being made of substantially flexible material, whereby said annular fin may be bent in a radially inward direction during insertion of the lens assembly into the eye while the ring-shaped frame member securely holds the optic member.

19. A lens assembly according to claim 18, wherein the lens member is composed of PMMA material and the frame member is composed of silicone material.

20. A lens assembly according to claim 18, wherein a portion of the ring-shaped frame member is substantially optically opaque.

21. A lens assembly according to claim 18, wherein a portion of the ring-shaped frame member is substantially optically translucent.

* * * * *